(12) United States Patent
Broze et al.

(10) Patent No.: US 12,370,070 B2
(45) Date of Patent: Jul. 29, 2025

(54) ORTHOSIS FASTENING SYSTEM

(71) Applicant: Spentys nv, Vorst (BE)

(72) Inventors: Louis-Philippe Broze, Vorst (BE); Florian De Boeck, Vorst (BE)

(73) Assignee: Spentys nv, Vorst (BE)

( * ) Notice: Subject to any disclaimer, the term of this patent is extended or adjusted under 35 U.S.C. 154(b) by 195 days.

(21) Appl. No.: 17/746,062

(22) Filed: May 17, 2022

(65) Prior Publication Data

US 2022/0370225 A1 Nov. 24, 2022

(51) Int. Cl.
*A61F 5/01* (2006.01)
*A43C 11/00* (2006.01)
*A61F 5/05* (2006.01)

(52) U.S. Cl.
CPC .............. *A61F 5/0104* (2013.01); *A61F 5/05* (2013.01); *A43C 11/00* (2013.01); *Y10T 24/21* (2015.01)

(58) Field of Classification Search
CPC ........... A43C 1/04; A43C 11/12; A43C 11/14; A43C 11/1406; A43C 11/1413; A43C 11/142; A43C 11/144; A43C 11/1446; A43C 11/1453; A43C 11/08; A43C 11/10; A43B 5/04; A43B 5/0433; Y10T 24/2106; Y10T 24/2142; Y10T 24/2183; Y10T 24/2187; Y10T 24/1422; A61F 5/0104; A61F 5/0106; A61F 5/0111; A61F 5/0118; A61F 5/04; A61F 5/05; A61F 5/055; A61F 5/058; A61F 5/05841; A61F 5/05883
See application file for complete search history.

(56) References Cited

U.S. PATENT DOCUMENTS

| | | | | | |
|---|---|---|---|---|---|
| 4,624,063 | A | * | 11/1986 | Delery | A43C 11/144 36/118.9 |
| 5,509,180 | A | * | 4/1996 | Benetti | A43C 11/148 24/71 SK |
| 5,836,902 | A | * | 11/1998 | Gray | A61F 5/0111 602/5 |
| 10,952,887 | B2 | * | 3/2021 | Lê | A61F 5/05866 |
| 2005/0165338 | A1 | | 7/2005 | Iglesias et al. | |
| 2010/0249684 | A1 | | 9/2010 | Spitzer | |
| 2017/0135839 | A1 | | 5/2017 | Ducharme et al. | |

FOREIGN PATENT DOCUMENTS

| | | |
|---|---|---|
| FR | 2776481 A1 | 10/1999 |
| WO | 2018195602 A1 | 11/2018 |
| WO | 2021004726 A1 | 1/2021 |

OTHER PUBLICATIONS

Extended European Search Report of corresponding EP application 21174425.5 mailed Nov. 8, 2022.

* cited by examiner

*Primary Examiner* — Keri J Nelson
(74) *Attorney, Agent, or Firm* — Vorys, Sater, Seymour and Pease, LLP

(57) ABSTRACT

The present invention relates to an orthosis (100) for bracing a body part. A first side (20) of the orthosis (100) comprises a connector element (1), and a second side (30) of the orthosis (100) comprising a receiving element (2). The connector and receiving elements (1, 2) together form a fastening system. The connector element (1) comprises a loop (3), wherein the receiving element (2) comprises a receiving component (4) adapted to receive said loop (3).

17 Claims, 3 Drawing Sheets

ORTHOSIS FASTENING SYSTEM

TECHNICAL FIELD

The present invention relates to an orthosis. In particular, the invention relates to an improved orthosis fastening system for bracing a body part.

BACKGROUND

Nowadays there are many methods and materials used in the field of orthosis, to keep body parts immobilized for some time, and to maintain a good alignment of bone segments. The commonly used traditional means to achieve this is gypsum. However, the preparation of gypsum is difficult and time-consuming, as well as limiting to the freedom of the user, as it cannot be swiftly removed and reapplied. Orthoses are replacing the use of traditional orthopedic means such as gypsum. However, one issue with the available orthoses is that they are not personalized per user. Adjusting means are available to fit said orthosis on said body part, however, adjusting said orthosis is often not easy. For example, it may require the use of two hands, therefore the user may not be able to adjust it themselves. Another problem is that said orthoses may cause the user to sweat, depending on the material they are made of and the ventilation provided. Another problem is that said orthoses may require some assembly steps before being ready for use. Another problem is that said orthoses may be made of rigid or semi-rigid materials e.g., not flexible materials, causing discomfort for the user in case of long-term use.

US 2017/135839 describes a brace comprising an elastomeric athletic or orthopedic brace, support for a joint complex and is an elastomeric sleeve having a distal portion and a proximal portion that surrounds and supports one or more joints and with fenestrations or cut-outs and optional supplemental supports or framework so as to provide an external anatomically configured network which augments the effects of the ligaments. The brace can be used prophylactically or therapeutically.

WO 2021/004726 relates to a closure for an orthosis, in particular a quick closure for an orthosis, having an attachment part and a retaining portion, wherein the attachment part is detachably fastened to the retaining portion. The attachment part has at least two tuck-in flaps, which are connected to each other at one first end on a base of the attachment part and delimit a receptacle region of the attachment part at two opposite sides. The retaining portion is designed such that, when the attachment part is fixed thereto, it is held in the receptacle region between the two tuck-in flaps. The retaining portion is part of a frame or a framework or a rail or another part of an orthosis and has at least one recess. One of the tuck-in flaps has at least one latching element which engages in the recess forming an indentation when the attachment part is slid onto the retaining portion WO 2018/195602 describes a plagiocephaly helmet for a patient. The helmet comprises a body comprising a front portion and a rear portion and defining a chamber to receive a head of the patient; an openable seam disposed in a wall of the body between the front portion and the rear portion of the body to allow for selective adjustment of a circumference of the body; and an adjustable closure for selective coupling together of the front portion and the rear portion at the openable seam.

US 2010/249684 describes a wrist support worn by a user can diminish or eliminate pain, stress, or discomfort on the wrist and hand regions while lifting various objects of size and weight in a repetitive or non-repetitive manner. To this end, the disclosed inventions generally seek to inhibit wrist extension and flexion, and ulnar and radial deviation, by means of a support that transfers forces around the wrist muscles and ligaments onto the larger and stronger muscles of the upper and lower arm.

US 2005/165338 describes an apparatus and method for providing an orthopaedic support having a flexible inner member and an exoskeleton that is molded directly onto the flexible inner member. One embodiment is a wrist support having a separate, attachable thumb spica, and may include a molded plastic exostructure supplying support for resisting motion of said wrist. An inner fabric support is attached to said molded exostructure for providing cushioning to the wrist area.

The present invention aims to resolve at least some of the problems mentioned above.

SUMMARY OF THE INVENTION

In a first aspect, the present invention relates to an orthosis for bracing a body part, according to claim 1. Preferred embodiments of the electrical assembly are provided in claims 2 to 12.

A first side of the orthosis comprises a connector element, and a second side of the orthosis comprises a receiving element. The connector and receiving elements together form a fastening system. The orthosis is characterized in that the connector element comprises a loop, wherein the receiving element comprises a receiving component adapted to receive said loop. It is an advantage of embodiments of the present invention that a medical orthosis is obtained. It is an advantage of embodiments of the present invention that a simple and robust fastening system is obtained. It is an advantage of embodiments of the present invention that a strong and reliable connection between said connector and receiving elements and the respective first and second sides of the orthosis is obtained, and therefore it is difficult to detach said connector and receiving elements and the respective first and second sides. It is an advantage of embodiments of the present invention that a resilient and durable orthosis design is obtained.

The receiving element may comprise multiple receiving components, each with a different distance to the edge of said second side. It is an advantage of embodiments of the present invention that the user is able to close and fasten the orthosis according to the desired size and shape of the body part to which the orthosis is attached. It is an advantage of embodiments of the present invention that an orthosis for users with body parts of different physical dimensions is obtained.

The connector element may comprise an elongate element extending longitudinally away from the first side of the orthosis. It is an advantage of embodiments of the present invention that a strong connection between the connector element and the first side is obtained. Said elongate element may be flexible. It is an advantage of embodiments of the present invention that a flexible connection between the connector element and the receiving element is achieved when fastening the orthosis. It is an advantage of embodiments of the present invention that the user him or herself is able to adjust said orthosis.

The loop may comprise two legs and a pin-like structure connectable between said legs to form a closed loop. It is an advantage of embodiments of the present invention that a rigid connection between the connector and receiving elements is obtained.

Said legs may be flexible. It is an advantage of embodiments of the present invention that the pin-like structure is connectable and removable between said legs. It is an advantage of embodiments of the present invention that a more flexible orthosis is obtained by making the connector and receiving elements of a flexible material.

A cavity on an inner side of each leg may be dimensioned to receive said pin-like structure. It is an advantage of embodiments of the present invention that once placed between the two legs, the pin-like structure is immobilized. It is an advantage of embodiments of the present invention that no assembly steps are needed, besides placing the pin-like structure between the two legs.

The receiving component may comprise at least two upstanding sections, wherein said pin-like structure is dimensioned to be received between said sections. It is an advantage of embodiments of the present invention that said pin-like structure is prevented from disengaging and escaping from between said sections without exercising a predetermined amount of force.

The receiving element may comprise blocking means laterally adjacent to said upstanding sections. It is an advantage of embodiments of the present invention that, after connecting the connector element to the receiving element, lateral movement of said connector element is prevented, and therefore a stable connection between said connector and receiving elements is obtained.

Any of the orthosis and the receiving element, or the orthosis and the connector element, or the orthosis and the receiving and connector elements may be manufactured, preferably 3D printed, in one piece, preferably using only one type of 3D printable material. It is an advantage of embodiments of the present invention that a fast and simple manufacturing process is achieved. It is an advantage of embodiments of the present invention that little or no post-processing is needed. It is an advantage of embodiments of the present invention that an orthosis of light weight is obtained. It is an advantage of embodiments of the present invention that the pin-like structure is not 3D printed, so as to provide a strong connection between said connector and receiving elements.

The connector element may comprise two or more pin-like structures. It is an advantage of embodiments of the present invention that the tension due to fastening is divided among different pin-like structures and different upstanding sections. It is an advantage of embodiments of the present invention that the lifetime of the connector and receiving elements is prolonged. It is an advantage of embodiments of the present invention that a more reliable and stronger connection between the connector and receiving elements is obtained.

The orthosis may have a mesh-like structure. It is an advantage of embodiments of the present invention that a more flexible orthosis is obtained. It is an advantage of embodiments of the present invention that good ventilation of the user's body part is obtained.

The orthosis may comprise two or more connector and receiving elements on the first and second sides. It is an advantage of embodiments of the present invention that the tension due to fastening is divided among different connector and receiving elements.

The orthosis may comprise multiple parts, each part comprising two or more connector and/or receiving elements, wherein each part is adapted to be connected to two or more parts via the connector and receiving elements. It is an advantage of embodiments of the present invention that it is possible to differently fasten different neighboring body parts, and therefore a more personalized fastening is obtained.

Further advantages of the invention and in particular of preferred embodiments are disclosed in the detailed description below.

DESCRIPTION OF THE FIGURES

FIG. 1 shows a connector element (1), a receiving element (2), and a pin-like structure (8), before connecting them to each other, according to embodiments of the present invention.

FIG. 2 shows a connector element (1), a receiving element (2), after connecting them to each other, according to embodiments of the present invention.

FIG. 3 shows a receiving element (2) on a second side (30), according to embodiments of the present invention.

FIGS. 4-5 show fastened orthoses (100), according to embodiments of the present invention.

DETAILED DESCRIPTION OF THE INVENTION

Figure 1:
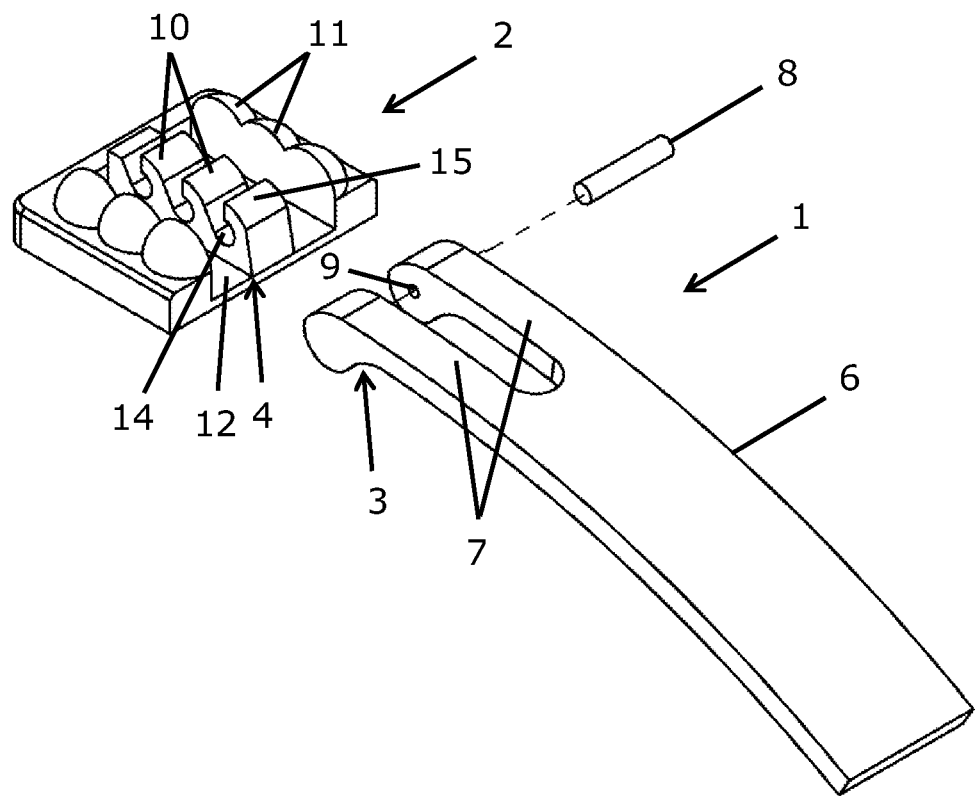
FIGS. 1-5 show orthoses (100) and components thereof for bracing a body part, according to embodiments of the invention.

The present invention relates to an orthosis for bracing a body part.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a contaminant" refers to one or more than one contaminant.

"Comprise", "comprising", and "comprises" and "comprised of" as used herein are synonymous with "include", "including", "includes" or "contain", "containing", "contains" and are inclusive or open-ended terms that specifies the presence of what follows e.g., component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

In a first aspect, the present invention relates to an orthosis for bracing a body part. A first side of the orthosis comprises a connector element, and a second side of the orthosis comprises a receiving element. The connector and receiving elements together form a fastening system. The orthosis is characterized in that the connector element comprises a loop, wherein the receiving element comprises a receiving component adapted to receive said loop. For example, the receiving component and the loop are complementary in shape and dimensions.

In a preferred embodiment, the orthosis may be used for medical purposes. The fastening system made by the connector and receiving element is simple and robust. For example, the user may adjust said fastening system themselves.

In a preferred embodiment, the surface that connects the connector element to the first side, and the receiving element to the second side, may substantially be large in size and strongly connected to avoid detaching said connector and receiving elements from the first and second sides, and therefore prolonging the lifetime of said orthosis. Preferably, the connector and receiving elements are single-piece with the first and second sides, and gradually transition into said first and second sides.

In a preferred embodiment, the receiving element may comprise multiple receiving components, each with a different distance to the edge of said second side. For example, the user is able to close and fasten the orthosis according to the desired size and shape, for example according to the body part to which the orthosis is attached, by choosing the appropriate receiving component. This allows the orthosis to be usable by users at multiple stages during a revalidation (when the body part to be braced is thinner or thicker) or even by multiple users who would normally require different size orthoses.

In a preferred embodiment, the receiving and connector elements, and other parts of the orthosis, may be flexible e.g., deformable. This allows the user to deform the connector element when connecting said element to the receiving element, providing an easily adjustable, customizable, and personalized orthosis depending on the physical shape and size of the body part of the user (e.g., a patient). This also prevents breaking of the receiving and connector elements when fastening the orthosis. It is also advantageous that the user him or herself may easily adjust said orthosis.

In a preferred embodiment, the connector element may comprise an elongate element extending longitudinally away from the first side of the orthosis. The elongate element is preferably flexible. This provides support to the connector element, for example preventing it from detaching from the first side, but also in giving the user increased flexibility in using the fastening system, as they can more easily manipulate the connector element. The elongate element also allows the connector element to have a flexible connection with the receiving element when fastening the orthosis.

In a preferred embodiment, the receiving and connector elements, and other parts of the orthosis, may be made of elastic e.g., stretchable material. For example, they may be made of a material that stretches by at least 2%, preferably at least 5%, more preferably at least 10%, yet more preferably at least 20%, even more preferably at least 30%, and again more preferably at least 40%, and most preferably at least 50%. This allows the user to stretch the connector element when connecting said element to the receiving element, providing an easily adjustable, customizable, and personalized orthosis depending on the physical shape and size of the body part of the user (e.g., a patient). This also prevents breaking of the receiving and connector elements when fastening the orthosis. It is also advantageous that the user him or herself may easily adjust said orthosis.

In a preferred embodiment, the length of said elongate element may be between 10 and 400 mm, preferably between 15 and 300 mm, more preferably between 20 and 200 mm.

In a preferred embodiment, the loop may comprise two legs, for example fork-like legs, and a pin-like structure connectable between said legs to form a closed loop. The two legs allow a higher flexibility than a 'full' strip, increasing ease of use. Said pin-like structure is preferably substantially rigid and comprises metal or a metal alloy or a composite. This is advantageous in providing a rigid and strong connection between said connector and receiving elements. For example, the pin-like structure may be made of steel or stainless steel. The pin-like structure may be made of a plastic material in case less forces are to be applied thereon i.e. when fastening the orthosis. Other rigid materials may be envisaged.

In a preferred embodiment, the loop may comprise at least two legs, for example three legs with two pin-like structure between each two adjacent legs. Alternatively, in the three leg configuration, one pin-like structure may be placed between the two outer legs, and through a hole in the middle leg.

In a preferred embodiment, said legs may be flexible. The pin-like structure has a predetermined length. Said legs are adapted to flexibly spread apart from each other by a distance longer than the length of the pin. For example, in order to fix the pin-like structure in between the two legs. For example, the legs may be adapted to spread apart to increase the width of the gap therebetween by at least 5%, preferably at least 10%. After releasing the legs, the pin-like structure is trapped between said legs. The pin-like structure may be replaced by another pin-like structure by spreading apart the legs, for example in case the pin-like structure needs to be replaced.

In a preferred embodiment, the legs may have a length between 5 and 300 mm, preferably between 10 and 210 mm, more preferably between 20 and 150 mm, most preferably between 50 and 100 mm. The width of the connector element, which is equal to the width of the two legs and the gap in between, may be between 5 and 200 mm, preferably between 10 and 100 mm, more preferably between 20 and 90 mm, most preferably between 30 and 80 mm. The width of each leg is between 3 to 20 mm, preferably between 5 to 16 mm, more preferably between 5.5 to 15.5 mm, most preferably between 7 and 13 mm.

In a preferred embodiment, the tip of each leg may have a semi-circular shape, with a diameter 5 to 20 mm, preferably between 10 and 15 mm.

In a preferred embodiment, the pin-like structure may be cylindrical, and it may further be hollow or solid. Said structure may also be rectangular or of any other suitable geometry. Said structure preferably does not bend with long use when connecting the connector to the receiving element. Said structure may have a diameter between 0.5 and 10 mm, preferably between 1 and 8 mm, more preferably between 2 and 6 mm, most preferably between 3 and 5 mm. The length of the pin-like structure is preferably essentially similar to the width of the gap between the two legs. For example, 2% wider than the width of the gap, preferably 5% wider, more preferably 10% wider, most preferably 15% wider.

In a preferred embodiment, the receiving element may be 5 to 200 mm wide in total, preferably 10 to 150 mm, more preferably 20 to 100 mm. The receiving element may further be 5 to 200 mm long in total, preferably 10 to 150 mm, more preferably 20 to 100 mm.

In a preferred embodiment, the thickness of the receiving and connector elements may be between 2 to 15 mm, preferably between 3.5 and 10 mm, more preferably between 4 and 7 mm.

In a preferred embodiment, a cavity on an inner side of each leg may be dimensioned to receive said pin-like structure. For example, the cavity and a tip of said pin-like structure are complementary in shape and dimensions, so as to receive one tip of the pin-like structure on the cavity of the inner side of each leg. For example, the depth of the cavity is less than 20% the width of the leg, preferably less than 10%, more preferably less than 5%. After placing the pin-like structure between the two legs, wherein each tip of the pin-like structure fits on the corresponding cavity, the pin-like structure is immobilized, and cannot be removed except by exercising a predetermined amount of force to spread the legs apart. Preferably, this is the only assembly step of said orthosis.

In a preferred embodiment, the receiving component may comprise at least two upstanding sections, wherein said pin-like structure is dimensioned to be received and trapped between said sections (e.g., or the upstanding sections are dimensioned to receive and trap the pin-like structure). Preferably, the upstanding sections extend substantially parallel to the second side of the orthosis. For example, a valley is formed between two consequent upstanding sections. For example, a cross-section of said valley is complementary in shape to a cross-section of the pin-like structure. For example, a circularly shaped valley is adapted to receive a circularly shaped pin-like structure. In a preferred embodiment, said sections comprise trapping means to prevent said pin-like structure from disengaging and escaping from between said sections without exercising a predetermined amount of force. For example, this is achieved by dimensioning the valley between the two upstanding sections to be substantially similar in shape and dimensions to the pin-like structure, for example, the pin-like structure having a diameter essentially similar to that of the valley. This is done to make it difficult for the pin-like structure to escape spontaneously from between the two upstanding sections when the orthosis is fastened e.g. without exercising a minimal amount of force by e.g. the fingers of the user.

In a preferred embodiment, since the receiving component is elastically deformable, the dimensions of the valley may further be the same or even slightly smaller than the pin-like structure, to keep said pin-like structure in place unless a predetermined amount of force is exercised to remove said pin-like structure from said valley.

In a preferred embodiment, the upstanding sections may be between 1 to 21 sections, for example, so as to receive the pin-like structure in 2 to 20 valleys. More preferably, the upstanding sections are between 3 to 10 sections, more preferably 3 to 4 sections. The upstanding sections are between 3 to 20 mm wide, preferably between 5 to 15 mm wide. The distance between every two consecutive sections is between 3 and 20 mm, preferably between 5 and 10 mm. The upstanding sections stick out from the receiving element by at least 3 mm, preferably by at least 5 mm.

In a preferred embodiment, the orthosis has a surface, wherein said sections may extend from the surface of the orthosis at least partly angled away from the edge of said second side (or towards said edge, depending on the position of the connector element). For example, the tip of each upstanding section is angled by at least 10°, preferably at least 25°, preferably at least 45°, for example forming a semi-circular bend, to prevent the pin-like structure from spontaneously escaping from between the sections e.g., when the orthosis is fastened. This way, the loop can be hooked behind the upstanding sections without risking to snap free under influence of tractive forces on the loop.

In a preferred embodiment, the receiving element may comprise blocking means laterally adjacent to said upstanding sections, for example, a right-hand side and a left-hand side blocking means. The blocking means and the upstanding sections are separated by a gap dimensioned to receive said legs of the connector element therebetween, for example a right-hand side gap, and a left-hand side gap, wherein the upstanding sections are in the middle of said gaps. Said gap is for example between 2 and 30 mm wide, preferably between 4 and 20 mm, more preferably between 5 to 15 mm. The blocking means are adapted to prevent, after connecting the connector to the receiving element, lateral movement of the legs with respect to the upstanding sections, so as to stabilize said legs, and therefore obtain a stable connection between said connector and receiving elements. The thickness of the receiving element at said gap is lower than the thickness of the receiving element at the blocking means or at the upstanding sections. For example, at least three times lower. For example, the thickness of the receiving element at the gap is between 0.5 to 2 mm. Said thickness difference is adapted such that the legs of the connecting element are received in said gap, wherein the blocking means are able to prevent the lateral movement of said legs. In a preferred embodiment, each of the right-hand side and left-hand side blocking means are between 4 to 20 mm wide, preferably between 5 to 15 mm.

In a preferred embodiment, the blocking means may comprise a series of hill-like structures or protrusion, for example one hill-like structure or protrusion adjacent to each two subsequent upstanding sections. Each of said hill-like structure or protrusion is shaped such that when said legs are received between said upstanding sections, said hill-like structure would prevent lateral movement of said legs. For example, each leg has a tip, wherein the tip has a semi-circular shape, wherein said hill-like structure is complementary in shape to the tip of said legs when said legs are received between said upstanding sections. Preferably, said blocking means are curved away from said upstanding sections, so as to avoid any sharp edges. The distance between each two consecutive hill-like structures is between 3 and 20 mm, preferably between 5 and 10 mm. The upstanding sections stick out from the receiving element by at least 3 mm, preferably by at least 5 mm.

In a preferred embodiment, the receiving element may comprise a flat surface between said upstanding sections and said blocking means, having a lower height than both. For example, said flat surface allows said legs to be received between said upstanding sections and said blocking means. For example, the difference in height between either of said upstanding sections or said blocking means, and said flat surface, matches the height of said legs.

In a preferred embodiment, said orthosis and components thereof (i.e. the connector and the receiving elements) may comprise a 3D printable material. Preferably, the orthosis and components thereof may comprise a thermoplastic, e.g. a thermoplastic polyurethane, and more preferably TPUMGF, due to its good flexibility. The orthosis and components thereof may alternatively comprise other materials such as TPULTM, and/or PA-11, and/or PA-12, and/or Resin ST45. For example, the orthosis and components thereof may be of the same or different material, preferably of only one material.

In a preferred embodiment, said orthosis and the elements thereof may be made using a 3D printing technique. For example, SLS, MJF, FFF, FDM, SLA, DLP, or CLIP. The orthosis is preferably light in weight.

In a preferred embodiment, the orthosis and the receiving element, or the orthosis and the connector element, or the orthosis and the receiving and connector elements may be manufactured, preferably 3D printed, in one piece (or two or more pieces), for example at once, using a 3D printer and a software therefor, preferably using only one type of 3D printable material. This allows to obtain a fast and simple manufacturing process. After printing, the pin-like structure is attached between said legs, said attachment being the only assembly step. In an alternative embodiment, the connector and receiving elements are printed and fixed or glued to any orthosis after printing said orthosis. Only little or no post-processing of the final printed product is needed.

In a preferred embodiment, the orthosis is modelled using a computer software in a 3D modeling step, and then 3D printed using a 3D printer, for example HP Multi Jet Fusion 3D printing technology.

In a preferred embodiment, the pin-like structure is not 3D printed. This provides a strong connection between said connector and receiving elements, since a 3D printed pin-like structure would be weaker than a rigid e.g., metallic pin-like structure. This allows to obtain a durable orthosis.

In a preferred embodiment, the connector element may comprise two or more pin-like structures. For example, said pin-like structures are parallel to each other, for example to be received by two (e.g., consecutive) receiving components. This is advantageous in obtaining a strong connection between the connector and receiving elements when fastening the orthosis. For example, to avoid breaking or bending of the pin-like structure in case of use over a long period of time, or in case the pin-like structure is not made of a sufficiently rigid material. On the other hand, this is also advantageous in avoiding to break the upstanding sections that are normally less rigid compared to the pin-like structures. Overall, this is advantageous in prolonging the lifetime of the orthosis and the components thereof, and provides a more reliable connection between the connector and receiving elements.

In a preferred embodiment, the orthosis may have a mesh-like structure. For example, the orthosis may have rectangular, oval, or circular meshes, for example at least 1 mesh per 10 cm$^2$, preferably at least 2, more preferably at least 3. This provides more flexibility to the orthosis, while also allowing a good ventilation to the user's body part and reducing the overall weight of the orthosis, increasing ease of use for the wearer.

In a preferred embodiment, the orthosis may comprise two or more connector and receiving elements on the first and second sides. This allows to divide the tension due to fastening among different connector and receiving elements. This also allows a more flexible operation, for example the user is free to use some of fasten some of the connector and receiving elements, and unfasten some others. Lastly, it allows the user to put on the orthosis, and then tighten up the connections one by one.

In a preferred embodiment, the orthosis may comprise multiple parts, each part comprising two or more connector and/or receiving elements, wherein each part is adapted to be connected to two or more parts via the connector and receiving elements. This allows for example to differently fasten different neighboring body parts, and therefore arriving at a more personalized fastening system. This can also be provided to allow for hinging orthoses.

In a second aspect, the present invention relates to a use of an orthosis according to the first aspect of the present invention for bracing a body part.

Further characteristics and advantages of embodiments of the present invention will be described with reference to the figure. It should be noted that the invention is not restricted to the specific embodiment shown in the figure, but is only limited by the claims.

FIGS. 1-5 show orthoses (100) and components thereof for bracing a body part.

A first side (20) of the orthosis (100) comprises a connector element (1), and a second side (30) of the orthosis (100) comprises a receiving element (2). The connector and receiving elements (1, 2) together form a fastening system. The connector element (1) comprises a loop (3), wherein the receiving element (2) comprises a receiving component (4) adapted to receive said loop (3). FIG. 1 shows the connector and receiving elements (1, 2) and a cylindrical pin-like structure (8), before connecting them to each other forming a closed loop (3).

The receiving element (2) comprises multiple receiving components (4), each with a different distance to the edge (5) of said second side (30).

The connector element (1) further comprises an elongate element (6) extending longitudinally away from said loop (3).

The loop (3) comprises two legs (7) and the pin-like structure (8). Said pin-like structure (8) is connectable (and removable) between said legs (7) to form a closed loop (3). The pin-like structure (8) is preferably substantially rigid and comprises a metal or a metal alloy or a composite.

The legs (7) are flexible, and the pin-like structure (8) has a predetermined length. The legs (7) are adapted to flexibly spread apart from each other by a distance higher than the length of the pin-like structure (8). A cavity (9) on an inner side of each leg (7) is dimensioned to receive said pin-like structure (8), for example the cavity is cylindrically-shaped.

The receiving component (4) comprises at least two upstanding sections (10). Said pin-like structure (8) is dimensioned to be received between said sections (10). Said sections (10) comprise trapping means (14) to prevent said pin-like structure (8) from disengaging from between said sections (10). For example, the means comprise a valley (14) in between each consequent upstanding section (10). For example, the valley (14) is dimensioned in shape and size to receive said pin-like structure (10).

The sections (10) extend from the surface of the orthosis at least partly angled away from the edge (5) of said second side (30), so as to make it more difficult for the pin-like structure (8) to escape. For example, a tip (15) of each upstanding section (10) is angled.

The receiving element (2) comprises blocking means (11) laterally adjacent to said upstanding sections (10). The blocking means (11) and the upstanding sections (10) are separated by a gap (12) dimensioned to receive said legs (7). The blocking means (11) comprises a series of hill-like structures or protrusion. For example, each hill-like structure (11) corresponds to two subsequent upstanding sections (10), and is shaped such that when said legs (7) are received between said upstanding sections (10), said hill-like structure (11) would prevent lateral movement of said legs (7).

Figure 2:
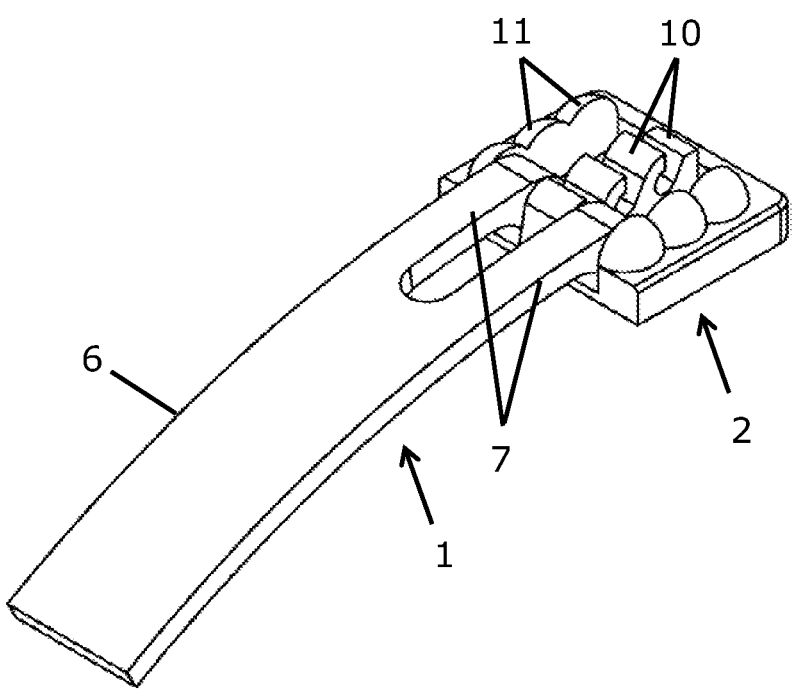

FIG. 2 shows the connector and receiving elements (1, 2), after connecting them to each other using the pin-like structure (8).

Figure 3:
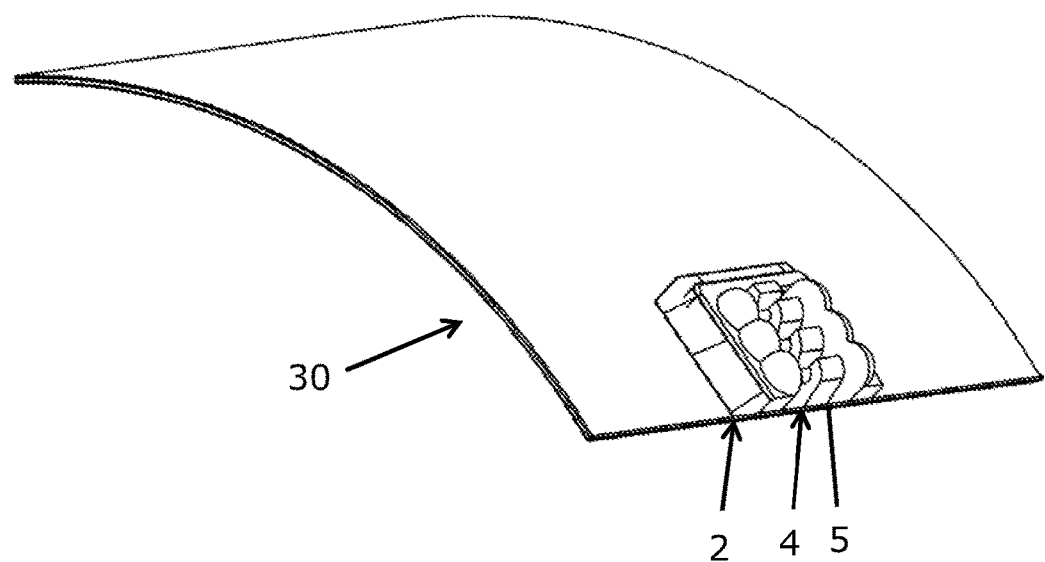

FIG. 3 shows a receiving element (2) on a second side (30), according to embodiments of the present invention.

The receiving element (2) is tangent to the surface of the orthosis, on said second side (30).

Figure 4:
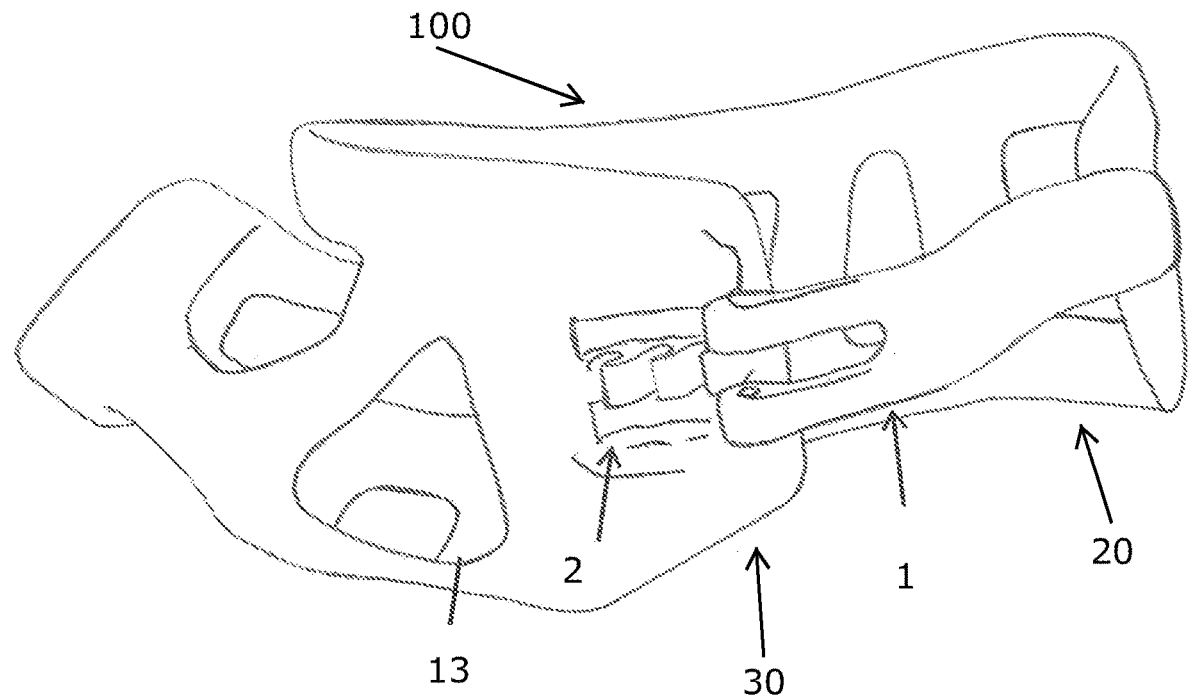
Figure 5:
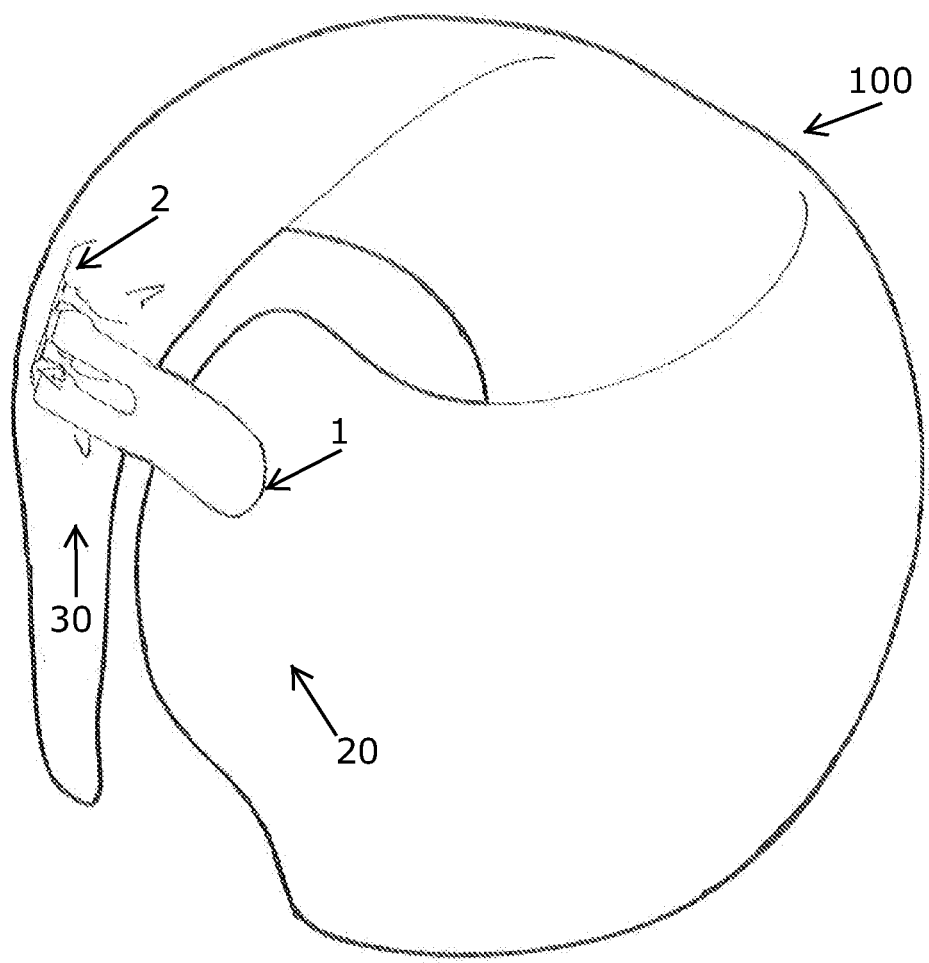

FIGS. 4-5 show fastened orthoses (100), for a hand/thumb (FIG. 4), and for a baby helmet (FIG. 5). Furthermore, the orthosis (100) in FIG. 4 has a mesh-like structure (13).

The preceding description gives details of certain embodiments of the present invention. It will, however, be clear that no matter how detailed the above turns out to be in text, the invention may be applied in many ways. It should be noted that the use of certain terminology when describing certain characteristics or aspects of the invention should not be interpreted as implying that the terminology herein is defined again to be restricted to specific characteristics or aspects of the invention to which this terminology is coupled.

The invention claimed is:

1. An orthosis for bracing a body part, wherein a first side of the orthosis comprises a connector element, and a second side of the orthosis comprises a receiving element, wherein the connector and receiving elements together form a fastening system,
   wherein the connector element comprises a loop, wherein the receiving element comprises a receiving component adapted to receive said loop,
   characterized in that the loop comprises two legs and a pin-like structure connectable between said legs to form a closed loop, wherein said pin-like structure comprises metal or a metal alloy or a composite and has a predetermined length,
   wherein the receiving component comprises at least two upstanding sections, wherein said pin-like structure is dimensioned to be received between said sections, wherein said sections comprise trapping means to prevent said pin-like structure from disengaging from between said sections,
   and wherein the receiving element comprises blocking means laterally adjacent to said upstanding sections, wherein the blocking means and the upstanding sections are separated by a gap dimensioned to receive the legs of the connector element,
   wherein said legs are flexible and are adapted to flexibly spread apart from each other by a distance longer than the predetermined length of the pin-like structure.

2. The orthosis according to claim 1, wherein said receiving element comprises multiple receiving components, each with a different distance to an edge of said second side.

3. The orthosis according to claim 1, wherein a cavity on an inner side of each leg is dimensioned to receive said pin-like structure.

4. The orthosis according to claim 1, wherein said sections extend from the surface of the orthosis at least partly angled away from an edge of said second side.

5. The orthosis according to claim 1, wherein the connector element further comprises an elongate element extending longitudinally away from the first side of the orthosis.

6. The orthosis according to claim 5, wherein the two legs extend from the elongate element away from the first side of the orthosis.

7. The orthosis according to claim 1, wherein said orthosis comprises a 3D printable material including a thermoplastic selected from the group consisting of TPUMGF, TPULTM, PA-11, PA-12, Resin ST45, and any combination thereof.

8. The orthosis according to claim 1, wherein the orthosis and the connector element, or the orthosis and the receiving element, or the orthosis and the connector and receiving elements are manufactured in one piece.

9. The orthosis according to claim 8, wherein the orthosis and the connector element, or the orthosis and the receiving element, or the orthosis and the connector and receiving element are 3D printed.

10. The orthosis according to claim 1, wherein the orthosis has a mesh-like structure.

11. The orthosis according to claim 1, wherein the orthosis comprises two or more connector and receiving elements on the first and second sides.

12. The orthosis according to claim 1, wherein the orthosis comprises multiple parts, each part comprising two or more connector and/or receiving elements, wherein each part is adapted to be connected to two or more parts via the connector and receiving elements.

13. The orthosis according to claim 1, wherein the upstanding sections have a width between 3 to 20 mm.

14. The orthosis according to claim 1, wherein the distance between every two consecutive upstanding sections is between 3 and 20 mm.

15. The orthosis according to claim 1, wherein the upstanding sections stick out from the receiving element by at least 3 mm.

16. The orthosis according to claim 1, wherein the receiving element comprises a flat surface between said upstanding sections and said blocking means, said flat surface having a lower height than the upstanding section and the blocking means, wherein said flat surface allows said legs to be received between said upstanding sections and said blocking means against the flat surface.

17. The orthosis according to claim 16, wherein the difference in height between either of said upstanding sections or said blocking means, and said flat surface, matches the height of said legs.

* * * * *